(12) United States Patent
Toledano et al.

(10) Patent No.: US 10,525,433 B2
(45) Date of Patent: Jan. 7, 2020

(54) FORMATION OF NANOMETRIC CORE-SHELL PARTICLES HAVING A METAL OXIDE SHELL

(75) Inventors: Ofer Toledano, Kfar Saba (IL); Hanan Sertchook, Gedera (IL); Raed Abu-Reziq, Jatt Hamesholash (IL); Haim Bar-Simantov, Modiin (IL); Leora Shapiro, Jerusalem (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 1952 days.

(21) Appl. No.: 12/518,743

(22) PCT Filed: Dec. 12, 2007

(86) PCT No.: PCT/IL2007/001541
§ 371 (c)(1),
(2), (4) Date: Mar. 15, 2010

(87) PCT Pub. No.: WO2008/072239
PCT Pub. Date: Jun. 19, 2008

(65) Prior Publication Data
US 2010/0203121 A1  Aug. 12, 2010

Related U.S. Application Data

(60) Provisional application No. 60/874,268, filed on Dec. 12, 2006.

(51) Int. Cl.
| *A61K 9/66* | (2006.01) |
| *A61K 8/06* | (2006.01) |
| *A61K 8/18* | (2006.01) |
| *A61Q 11/00* | (2006.01) |
| *A61Q 17/04* | (2006.01) |
| *B01J 13/14* | (2006.01) |

(52) U.S. Cl.
CPC ..................... *B01J 13/14* (2013.01)

(58) Field of Classification Search
CPC ....................................... B01J 13/14
USPC ....................................... 424/455
See application file for complete search history.

(56) References Cited

U.S. PATENT DOCUMENTS

| 4,931,362 | A  | 6/1990  | Zsifkovits et al. |
| 6,238,650 | B1 | 5/2001  | Lapidot et al. |
| 6,251,313 | B1 | 6/2001  | Deubzer et al. |
| 6,303,149 | B1 | 10/2001 | Magdassi et al. |
| 6,337,089 | B1 | 1/2002  | Yoshioka et al. |
| 6,436,375 | B1 | 8/2002  | Lapidot et al. |
| 6,468,509 | B2 | 10/2002 | Lapidot et al. |
| 6,855,335 | B2 | 2/2005  | Seok et al. |
| 2002/0064541 | A1 | 5/2002 | Lapidot et al. |
| 2005/0037087 | A1 | 2/2005 | Lapidot et al. |

FOREIGN PATENT DOCUMENTS

| EP | 0 934 773 | 8/1999 |
| EP | 0 941 761 A2 | 9/1999 |
| GB | 2 416 524 A | 2/2006 |
| JP | A-2001-106612 | 4/2001 |
| WO | WO 00/09652 A2 | 2/2000 |
| WO | WO 00/71084 A1 | 11/2000 |
| WO | WO 00/72806 A2 | 12/2000 |
| WO | WO 01/80823 A2 | 11/2001 |
| WO | WO 03/003497 A1 | 1/2003 |
| WO | WO 03/034979 A2 | 5/2003 |
| WO | WO 03/039510 A1 | 5/2003 |
| WO | WO 03/066209 A1 | 8/2003 |
| WO | WO 2004/081222 A2 | 9/2004 |
| WO | WO 2005/009604 A1 | 2/2005 |
| WO | WO 2007/000316 A1 | 1/2007 |
| WO | WO 2008/002637 A2 | 1/2008 |

OTHER PUBLICATIONS

Suryanarayanan et al. Electrochemical investigations of oxide coated nanoparticles. Proc. Indian Natn. Sci. Acad. 70A (3), pp. 483-488 (2004).*
International Search Report issued in International Patent Application No. PCT/IL2007/001541 dated Jul. 10, 2008.
Written Opinion on Patentability issued in International Patent Application No. PCT/IL2007/001541 dated Jul. 10, 2008.

\* cited by examiner

*Primary Examiner* — Mina Haghighatian
*Assistant Examiner* — Mei Ping Chui
(74) *Attorney, Agent, or Firm* — Mark S. Cohen; Pearl Cohen Zedek Latzer Baratz LLP

(57) ABSTRACT

A process for preparing nanocapsules having a core-shell structure, comprising:
(a) preparing an oil-in-water emulsion by emulsification of an oily phase that comprises a core material, in an aqueous phase, under high shear forces, wherein one or both of the oily phase, and the aqueous phase comprises a sol-gel precursor; (b) subjecting the emulsion obtained in (a) to a high pressure homogenization to obtain a nano-emulsion; and (c) applying conditions for hydrolyzing and polycondensing the sol-gel precursor to obtain nanocapsules having a metal oxide shell encapsulating the core material, said nanocapsules have a particle size distribution of: d10=10-80 nm, d50=30-200 nm, and d90=70-500 nm, in diameter. The invention also relate to nanocapsules having the above particle size distribution and to composition comprising the nanocapsules.

20 Claims, 2 Drawing Sheets

| Results | | Diam.(nm) | % Intensity | Width (nm) |
|---|---|---|---|---|
| Z-Average (d.nm): 53.9 | Peak 1: | 84.2 | 100.0 | 60.7 |
| PdI: 0.349 | Peak 2: | 0.00 | 0.0 | 0.00 |
| Intercept : 0.750 | Peak 3: | 0.00 | 0.0 | 0.00 |

| Results | | Diam.(nm) | % Intensity | Width (nm) |
|---|---|---|---|---|
| Z-Average (d.nm): 42.0 | Peak 1: | 67.9 | 99.4 | 49.2 |
| PdI: 0.382 | Peak 2: | 3980 | 0.6 | 1090 |
| Intercept : 0.674 | Peak 3: | 0.00 | 0.0 | 0.00 |

FORMATION OF NANOMETRIC CORE-SHELL PARTICLES HAVING A METAL OXIDE SHELL

CROSS REFERENCE TO RELATED APPLICATIONS

This application is a National Phase Application of PCT International Application No. PCT/IL2007/001541, International Filing date Dec. 12, 2007, which claims the benefit of U.S. Provisional Application 60/874,268 filed Dec. 12, 2006, which is hereby incorporated by reference.

FIELD OF THE INVENTION

This invention relates to nanocapsules and a method for their preparation.

BACKGROUND OF THE INVENTION

Microcapsules composed of a shell prepared by a sol-gel process has been described in various publications:

U.S. Pat. Nos. 6,303,149, 6,238,650, 6,468,509, 6,436,375, US2005037087, US2002064541, and International publication Nos. WO 00/09652, WO00/72806, WO 01/80823, WO 03/03497, WO 03/039510, WO00/71084, WO05/009604, and WO04/81222, disclose sol-gel microcapsules and methods for their preparation. EP 0 934 773 and U.S. Pat. No. 6,337,089 teach microcapsules containing core material and a capsule wall made of organopolysiloxane, and their production. EP 0 941 761 and U.S. Pat. No. 6,251,313 also teach the preparation of microcapsules having shell walls of organopolysiloxane.

U.S. Pat. No. 4,931,362 describes a method of forming microcapsules or micromatrix bodies having an interior water-immiscible liquid phase containing an active, water-immiscible ingredient. As a capsule-forming or matrix-forming monomer, an organosilicon compound is used.

Microcapsules prepared by a sol-gel process are also disclosed in GB2416524, U.S. Pat. No. 6,855,335, WO03/066209.

Such microcapsules have use in various applications where chemical contact between the active ingredient and the immediate environment should be minimized, e.g. colorants for cosmetics, food colors, sunscreen compositions or in other applications where delivery of the active ingredient is of benefit (e.g. topical delivery onto the skin). However, for certain applications such as parenteral administration, oral administration, textile industry, it will be highly advantageous to have nanocapsules, particularly having a narrow size distribution, which are inert, simplified in production, can be easily incorporated in various carriers, which are capable of isolating and/or releasing the active ingredient therefrom, depending on the intended use, and yet which are physically stable during storage (e.g. do not form agglomerates, preferably do not form agglomerates even in compositions substantially free of surfactants) thereby providing long term use of the formulation.

BRIEF DESCRIPTION OF THE DRAWINGS

FIG. 2 shows the nanocapsules obtained according to example 2 analyzed by transmission electron microscope (TEM).

SUMMARY OF THE INVENTION

Figure 1A:
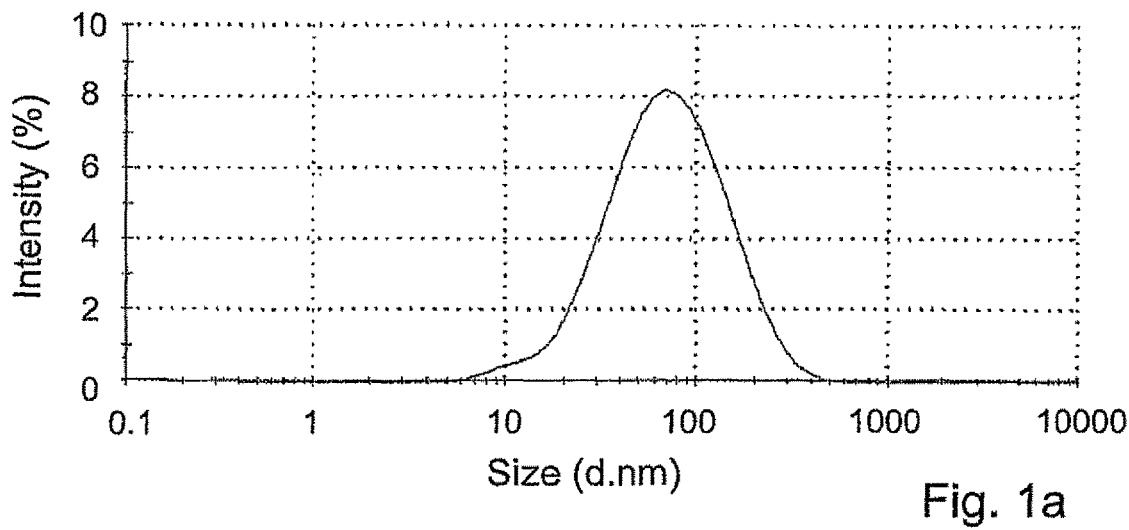
FIG. 1 shows particle size distribution of the nanocapsules measured by dynamic light scattering obtained by Example 1 (FIG. 1A) and Example 2 (FIG. 1B).

According to one aspect of the present invention there is provided a process for preparing nanocapsules having a core-shell structure, comprising:
 (a) preparing an oil-in-water emulsion by emulsification of an oily phase that comprises a core material, in an aqueous phase, under high shear forces, wherein one or both of the oily phase, and the aqueous phase comprises a sol-gel precursor;
 (b) subjecting the emulsion obtained in (a) to a high pressure homogenization to obtain a nano-emulsion; and
 (c) applying conditions for hydrolyzing and polycondensing the sol-gel precursor to obtain nanocapsules having a metal oxide shell encapsulating the core material, said nanocapsules have a particle size distribution of: d10=10-80 nm, d50=30-200 nm, and d90=70-500 nm, in diameter.

According to another aspect of the present invention there is provided product obtained by the process as described in the present invention.

According to a further aspect of the present invention there is provided nanocapsules having a core material encapsulated within a nanocapsular shell, the nanocapsular shell comprises at least one metal oxide, and wherein the nanocapsules have a particle size distribution of: d10=10-80 nm, d50=30-200 nm, d90=70-500 nm, in diameter.

According to an additional aspect of the invention there is provided a composition comprising nanocapsules as described in the present invention, and a carrier.

DETAILED DESCRIPTION OF THE INVENTION

The present invention is based on the finding that it is possible to prepare by a sol-gel process nanocapsules having a metal oxide shell, which are characterized by narrow particle size distribution. Such nanocapsules are advantageous for applications where narrow size distributions in the nano-scale size are of benefit such as for incorporation into fibers (e.g for use in textile), dispersion in matrices (such as UV stabilizers of polyolefin matrices), cosmetics, and pharmaceutical applications (e.g. parenteral administration). The nanocapsules obtained were found to be physically stable during storage (in an aqueous medium free of surfactants) and did not undergo agglomeration.

The present invention relates to a process for preparing nanocapsules having a core-shell structure, comprising:
 (a) preparing an oil-in-water emulsion by emulsification of an oily phase that comprises a core material, in an aqueous phase, under high shear forces, wherein one or both of the oily phase, and the aqueous phase comprises a sol-gel precursor;
 (b) subjecting the emulsion obtained in (a) to a high pressure homogenization to obtain a nano-emulsion; and
 (c) applying conditions for hydrolyzing and polycondensing the sol-gel precursor to obtain nanocapsules having a metal oxide shell encapsulating the core material, said nanocapsules have a particle size distribution of: d10=10-80 nm, d50=30-200 nm, and d90=70-500 nm, in diameter.

It has been found that it is possible to obtain nonocapsules, prepared by a sol-gel process, having a narrow particle size distribution and yet which are physically stable (e.g. which do not form agglomerates) by a process utilizing high shear forces and high pressure homogenization.

As used herein the term "core material" refers to the material constituting the inner part (core) of the nanocapsules optionally comprising an active ingredient. The core material is surrounded by the shell of the nanocapsules. This term refers to any material present in the core, e.g. both the active ingredient and the excipients such as the liquid carrier, or the excipients in case an active ingredient is absent. This term will also be used to define the material incorporated into the oily phase of the emulsion used in the process described herein that will subsequently constitute the core of the nanocapsule.

The core material may include as an excipient a liquid hydrophobic core material e.g. oils. The oils may be cosmetically acceptable (depending on the intended application) and may be for example alkanes, alkenes, glycerides or triglycerides, fatty alcohols, fatty acids and fatty acids esters like dicaprylyl maleate, Capric triglyceride, caprylic triglyceride, octyl palmitate, $C_{12}$-$C_{15}$ alkyl benzoate, dioctyl maleate, dioctyl malate, propylene glycol dicaprylate, propylene glycol dicaprate, diisopropyl adipate, hexyl laurate, lanolin, natural or synthetic oils and waxes, and mixtures thereof. It is appreciated that other excipients may be used depending on the intended use of the nanocapsules, the nature of the active ingredient, etc.

As used herein the term "high shear forces" is meant energy applied by mixers or disperses in order to transport one phase (oily phase) into a main continuous phase (aqueous phase), with which it would normally be immiscible to obtain an emulsion, typically having a median particle (droplet's) size of d50=1-20 μM. The high energy dispersing process can be conducted by high shear mixing or by high energy milling. This phase transport is accomplished by an input of energy, usually through high speed dispersing units such as an electric motor and rotating propeller or high speed rotor. Preferably the high speed dispersing units work at a shearing rate in the range of 0.1-40 m/sec, more preferably 2-8 msec, even more preferably 5-8 m/sec, typically using dispersing aggregates PT-DA 6045/6 and utilizing a high shear homogenizer—e.g. Polytron PT6100, Kinematica. It is appreciated that the particle size also depends on the type of oil used in the preparation of the emulsion.

As used herein the term "high pressure homogenization" refers to the creation of a high concentration of energy which is released on the processed emulsion. This high pressure (energy) creates a number of fluid mechanical effects like cavitations, turbulence, shear and impact which result in a homogeneous nano-droplet size distribution. The process may be carried out through a valve (homogenizing valve) or by milling cells, with application of a pressure, typically in the range of 1000-2000 bar, preferably 1300-1700 bar. An example of high pressure homogenizer is Microfluidizer.

Thus, for example in the process of the present invention, homogenizing the emulsion may be conducted by high shear homogenizer (Polytron PT 6100 Kinematica) with dispersing aggregates PT-DA 6045/6 in 1000-4000 rpm (preferably 3000 rpm) for about 1-10 min (preferably about 5 min). The dispersion is then homogenized in a high pressure homogenizer (e.g. M-110Y microfluidizer processor (Microfluidics) for about 5-30 min (preferably about 10 min).

As used herein the terms d10, d50 and d90 relate to the diameter of 10%, 50% and 90% by volume of the particles, respectively. For example, the designation d10=10-80 nm, indicates that 10% by volume of the particles (i.e. the nanocapsules) have a diameter less than or equal to a value within the indicated range of 10 to 80 nm. Similarly the designation d50=30-200 nm means that 50% by volume of the particles have a diameter less than or equal to a value within the range of 30 to 200 nm; the designation d90=70-500 nm means that 90% by volume of the particles have a diameter less than or equal to a value within the range of 70 to 500 nm; etc.

As used herein the terms "d10" and "d(0.1)", "d50" and "d(0.5)", "d90" and "d(0.9)" has the same meaning and will be used interchangeably.

According to a preferred embodiment of the present invention the difference between d90 and d10 (d90-d10) is preferably in the range 50-300 nm, more preferably in the range 50-250 nm, even more preferably in the range 50-200 nm, and most preferably in the range 50-150 nm.

Particle size distribution by volume is typically measured by methods such as light scattering (e.g. dynamic light scattering) or laser diffraction.

According to one embodiment the emulsion in step (a) is characterized by having a median particle (droplet) size diameter (d50) in the range 1-10 μm.

According to a specific embodiment the emulsion in step (a) has a particle size distribution (of droplets) of d10=0.5-5 μm, d50=1-10 μm, d90=2-30 μm, in diameter.

The parameters d10, d50, d90 referred to above with respect to the emulsion has the same meaning as defined above with respect to the nanocapsules.

As used herein the term "d10=0.5-5 μm", indicates that 10% by volume of the particles (droplets) size (in diameter) is less than or equal to a value in the range 0.5-5 μm.

As used herein the term "d50=1-10 μm", indicates that 50% by volume of the particles (droplets) size (in diameter) is less than or equal to a value in the range 1-10 μm.

As used herein the term "d90=2-30 μm", indicates that 90% by volume of the particles (droplets) size (in diameter) is less than or equal to a value in the range 2-30 μm.

According to a preferred embodiment the oily phase comprises the sol-gel precursor.

Thus, according to this preferred embodiment step (a) comprises (a) preparing an oil-in-water emulsion by emulsification of an oily phase that comprises a core material and a sol-gel precursor in an aqueous phase under high shear forces.

As used herein, the term "sol-gel precursor" refers to any organo-metallic or organo semi-metallic monomer, or a prepolymer (which means several monomers polymerized together) thereof, which allows to obtain a metal oxide material (e.g. silica) by in-situ polymerization (an inorganic sol-gel polymerization process).

As used herein, the term "in situ polymerization" refers to the sol-gel polymerization process of a sol-gel precursor forming an inorganic polymer at the oil-water interface of the emulsion as a result of the hydrolysis and condensation reactions of the sol-gel precursor.

Preferably the sol-gel precursors are selected from metal alkoxide monomers, semi-metal alkoxide monomers, metal ester monomers, semi-metal ester monomers and from monomers of the formula $M(R)_n (P)_m$, wherein M is a metallic or semi metallic element, R is a hydrolysable substituent, n is an integer from 2 to 6, P is a non polymerizable substituent and m is and integer from 0 to 6, a partially hydrolyzed and partially condensed polymer thereof, or any mixture thereof.

Preferably the metallic or semi metallic element is selected from Si, Ti, Zr, Al, and Zn.

According to a preferred embodiment of the present invention R (i.e. the hydrolysable substituent) is selected from an $C_1$-$C_6$alkoxy, an aryloxy, a carboxylic ester, an acyloxy group, a halo (e.g. chloro or bromo).

By the term "$C_1$-$C_6$alkoxy" is meant that the alkyl of the alkoxy is a $C_1$-$C_6$ alkyl, more preferably $C_1$-$C_4$ alkyl and most preferably a methyl or ethyl.

Preferably the aryl of the aryloxide is a phenyl group.

P (i.e. the non polymerizable substituent) may be for example $C_1$-$C_{18}$alkyl, aryl, aryl $C_1$-$C_{18}$alkyl, $C_1$-$C_{18}$alkyl amine, $C_1$-$C_{18}$alkyl methacrylate, halo$C_1$-$C_{18}$alkyl, allyl, vinyl, $C_1$-$C_{18}$alkyl ester, acryloxy, allyloxy, aryloxy, carboxy$C_1$-$C_{18}$alkyl, $C_1$-$C_{18}$alkyl(C=O)—O—, cyano$C_1$-$C_{18}$alkyl, epoxycycloalkyl, glycidoxyalkyl, methacryloxy, mercapto group.

It is appreciated that by the term "non polymerizable substituent" is meant that said non polymerizable substituent does not undergo hydrolysis (i.e. in the M-P bond) in the conditions used to prepare the nanocapsules (i.e. the sol-gel process conditions used to prepare the nanocapsules' shell). By this term is further meant that the non polymerizable substituent does not undergo polymerization in the conditions used to prepare the nanocapsules (i.e. the sol-gel process).

The sol-gel precursor may be a single monomeric unit or alternatively the sol-gel precursor may be comprised of a number of monomeric units (at times also referred to as "prepolymer").

For example, the precursor may be an oligomer of the precursor for example, a prehydrolyzed tetraethoxy silane (TEOS) which is based on the hydrolysis of TEOS, which may be used in order to obtain short chain polymers (prepolymer) that can also be used for encapsulation.

In a specific embodiment of this invention, the sol-gel precursors are selected from silicon alkoxide monomers, silicon ester monomers, monomers of the formula $Si(R)_n(P)_m$, where R is a hydrolysable substituent, n is an integer from 2 to 4, P is a non polymerizable substituent and m is and integer from 0 to 2, a partially hydrolyzed and partially condensed polymer thereof, and any mixture thereof.

R and P may be as defined above. According to a preferred embodiment m=0 and n=4. Preferably R is a $C_1$-$C_6$ alkoxy, more preferably $C_1$-$C_4$ alkoxy, and most preferably R is an ethoxy or methoxy group. In another embodiment of this invention, several precursors are used together in the oil phase as a mixture of several metals or semi metal monomers, to afford a nanocapsule shell which is a composite including different metal and/or semi metal elements in the final product.

Preferably the precursor is selected from metal alkoxide monomer, semi metal alkoxide monomer, a partially hydrolyzed and partially condensed polymers thereof, and any mixture thereof.

Preferably the semi metal alkoxide monomer is silicon alkoxide monomer.

Preferably the silicon alkoxide monomer is selected from tetramethoxy silane (TMOS), tetraethoxy silane (TEOS), and mixtures thereof.

Most preferably the silicon alkoxide monomer is tetraethoxy silane.

The sol-gel precursors which may be used in the present invention (termed also sol-gel precursors) are also described in U.S. Pat. Nos. 6,303,149, 6,238,650, 6,468,509, 6,436,375 and International Publication Nos. WO 01/80823, WO 03/034979 and WO 03/039510 (the disclosures of these patents and publications are incorporated herein by reference in their entirety).

According to one embodiment the conditions in step (c) comprising adding a catalyst to accelerate the formation of the nanocapsular shell for example, by adding an acid or a base.

Thus, according to a preferred embodiment the conditions in step (c) comprising adding a catalyst selected from an acid or base. In a preferred embodiment the acid is added to provide the nano-emulsion a pH in the range 2-5. In another embodiment a base is added to provide the nano-emulsion a pH in the range 8-13.

Thus, the conditions in step (c) may comprise for example mixing and stirring the nano emulsion with another aqueous solution at a suitably selected pH in the range of 2-13, preferably to obtain a pH of 2-5 or 8-13 of the nano-emulsion, more preferably to obtain a pH of 2-5 of the nano-emulsion, even more preferably a pH of 3-4, so as to form nanocapsules in a suspension.

According to a preferred embodiment the pH of the aqueous solution is in the range of 2-5, even more preferably 3-4.

The pH of the aqueous phase in step (a) may be in the range 2-13. According to one embodiment the pH of the aqueous phase in step (a) may be in the range 2-5. In accordance with this embodiment, the conditions in step (c) may be allowing nanocapsules formation (without adding a catalyst) optionally with stirring until nanocapsules are formed.

According to a preferred embodiment the pH of the aqueous phase in step (a) is in the range of 5-8.

In certain embodiments in case the aqueous phase of the emulsion has a pH in the range 2-5, more specifically 3-4, nanocapsules in suspension may be obtained after the nano-emulsification step without the need of further processing, e.g. adding a catalyst such as an acid or base. In such a case the conditions in step (c) may be allowing nanocapsules formation (with optionally mixing of the nano-emulsion) without further treatment to accelerate hydrolysis and polycondensation.

Preferably the conditions in step (c) comprise mixing the nano-emulsion.

The mixing in step (c) may be conducted for at least 4 hours, typically 4-24 hours. An indication for the completion of the reaction and nanocapsules' formation is obtaining constant loss on drying value, upon repeated measurements of samples of the nanocapsules taken form the reaction medium.

Preferably in step (a) one of the aqueous phase, oily phase, or both includes a surfactant.

Preferably the aqueous phase in step (a) includes a surfactant.

The process may further comprise adding a catalyst in step (a). The process may further comprise the step of adding an ingredient selected from a surfactant, a catalyst, and a mixture thereof in step (a). The surfactant may be selected from a cationic surfactant, an anionic surfactant, a non-ionic surfactant and mixtures thereof.

Preferably the surfactant is a cationic surfactant. Most preferably the cationic surfactant is cetyltrimethyl ammonium chloride (CTAC).

Preferably the catalyst is an acidic solution such as a hydrochloric acid solution, phosphoric acid solution or nitric acid solution. The catalyst may also be a salt like sodium fluoride (NaF), ammonium fluoride, and mixtures thereof.

The hydrophobic oily phase and/or the aqueous phase may include additional surfactants or any additives to improve the product.

The surfactant may be for example an anionic surfactant, a cationic surfactant, a non-ionic surfactant, an anionic polymeric surfactant, a cationic polymeric surfactant, a non-ionic polymeric surfactant, or mixtures thereof.

The emulsification may be performed using at least one emulsification agent (surfactant). The aqueous solution may comprise at least one hydrophilic (water soluble) surfactant.

The oily phase may comprise a hydrophobic surfactant, hydrophobic polymeric surfactant, or mixtures thereof. Preferably the hydrophobic surfactant or hydrophobic polymeric surfactant is a non-ionic surfactant.

The hydrophilic surfactant may be for example an anionic, a cationic, a non-ionic surfactant, or mixtures thereof.

According to a preferred embodiment the emulsification is preferably performed using at least one hydrophilic surfactant. Preferably the hydrophilic surfactant is a cationic surfactant.

Most preferably the cationic surfactant is cetyltrimethyl ammonium chloride (CTAC).

The concentration of the cationic surfactant in the aqueous solution (aqueous phase) may be from 0.1 to 5% (w/w) and more preferably from 1 to 5% (w/w). It is appreciated that the concentration of the surfactant will also depend on the percentage of the oily phase and aqueous phase. The concentration of the surfactant may be 5-10% (w/w) from the weight of the oily phase.

The process of the present invention may further comprise the step of isolating and rinsing the nanocapsules through procedures selected from at least one of separation by centrifuge; filtration; evaporation; re-suspension in_an aqueous medium; and dialysis.

The process of the present invention may further comprise an additional step of isolating and rinsing the nanocapsules through cycles selected from separation by centrifuge or by filtration and re-suspension in water, evaporation and re-suspension in water or by dialysis or by any other conventional means known in the art.

The suspension so obtained may be stabilized by adding additives such as non-ionic, cationic or anionic polymers or surfactants or mixtures thereof. The suspension may be stabilized by any other suitable suspending agent to obtain the final product in a suspension form.

The process may further comprise the step of removing the water (such as evaporation filtration etc.) to obtain the final product (nanocapsules) in a powder form.

The process may further comprise the step of adding-reconstitution additives such as non-ionic, cationic or anionic surfactants or polymers, or mixtures thereof. (The surfactants or polymers may be non-ionic, cationic or anionic).

It has been surprisingly found that the nanocapsules of the present invention are physically stable for a period of time of three months, in an aqueous medium substantially free of surfactants, at ambient conditions, with an increase of about 10% in particle size parameters (d10, d50, d90). By the term "substantially free of surfactants" is meant that only negligible amount of surfactant originating from the emylsification process (used in preparation of the emulsion) may be present.

Preferably the nanocapsules are physically stable in a liquid or semi-solid composition for a period of 3 month, more preferably for 1 year (preferably for 3 months to one year) and most preferably for 3 years (preferably 3 months to 3 years), at ambient temperature. Preferably the composition is substantially free of surfactant.

By the term "physically stable" is meant an increase of up to 30% in diameter, preferably up to 20% and more preferably up to 10% of the parameters d10, d50, and d90.

Preferably the process is carried out at a temperature between 4-40° C. Step (a) is preferably carried out at a temperature of 20-25° C.; step (b) is preferably carried out at a temperature of 5-25° C., more preferably 5-15° C., even more preferably 5-10° C.; Step (c) is preferably carried out at a temperature of 4-35° C., more preferably 15-25° C.

The nano-emulsion obtained in step (b) and/or the nanocapsules obtained in step (c) may further comprise an additional step selected from: heating, cooling, subjecting to vacuum or pressure, keeping under inert gas atmosphere, subjecting to changes in pH, and subjecting to an aging period.

As used herein, the term "aging" refers to the period of time added over the end of the nanocapsular shell (metal oxide-shell) formation, needed in order to obtain the smallest leaching rate of the active ingredient due to closure of the open pores of the shell.

In one embodiment the product obtained by the process is a suspension of said nanocapsules.

In another embodiment the product obtained is a powder of said nanocapsules. When the product obtained is a powder of said nanocapsules, the process further comprises a further step of removing the water by any means known in the art such as evaporation, filtration, freeze drying etc.

The process may further comprise the step of dispersing the obtained nanocapsules in a carrier.

The carrier may be for example a cosmetic carrier, a pharmaceutical carrier, a food carrier, a carrier used in agriculture or industrial processes.

The carrier may be for example a liquid, a semi solid or a solid carrier.

Incorporation of the final product either in the form of a suspension or a powder in cosmetic or pharmaceutical formulations can improve the bioavailability of the cosmetic or pharmaceutical actives ingredients thus retaining a reservoir of active ingredients to prolong duration of action.

The process of the present invention may further include the step of modifying the surface charge of the products by adding anionic or cationic surfactants or polymers during any step of the process.

The emulsion obtained in step (a) and/or the nano emulsion obtained in step (b) may be heated or cooled, subject to vacuum, or pressure, or kept under inert gas atmosphere, subject to changes in pH, or subject to an optional further aging period at room or accelerated temperature.

The resulting particles (nanocapsules) can be optionally isolated and rinsed through cycles of centrifuge or filtration and re-suspension in deionized water or by dialysis or by any other technique known in the art.

The obtained suspension may be incorporated for example into a suitable carrier.

The final product may also be used in a powder form, after removal of the water by appropriate means (such as drying, lyophilization, etc.) with optional addition of reconstitution additives such as non-ionic, cationic or anionic surfactants or polymers.

The concentration of the oily phase in the emulsion may be in the range 5% to 80% (w/w), more preferably in the range 10-60%.

Preferably the weight ratio of the sol-gel precursors to the core material is from 5/95 to 50/50. More preferably the weigh ratio of the sol-gel precursors to the core material is from 15/85 to 70/30. The above ratios relate to tetraethoxy silane (TEOS) as a precursor. The weight ratios when using other precursors can be calculated on mole basis.

The concentration of the core material based total weight of the nanocapsules may be from 20% to 98% (w/w). According to a specific embodiment the concentration of the core material based total weight of the nanocapsules is from 50% to 95% (w/w).

Preferably the core of the nanocapsules obtained is a liquid core. More preferably the liquid core is an oily core for example in the form of a solution, suspension or dispersion.

According to one embodiment the oily phase comprising the sol-precursor and the core material (including the active ingredient) are water immiscible.

According to certain embodiments the sol-gel precursor and the core material are mixed before emulsification. According to other embodiments the core material is emulsified in an aqueous phase to which a sol-gel precursor was added (before or after emulsification).

The active ingredient may be any molecule or substance that is soluble or that can be suspended in the sol-gel precursor (metal or in the semi metal alkoxides) of choice.

The nanocapsular shell formed comprises at least one metal oxide comprising polymerized sol-gel precursors obtained by in-situ polymerization of the sol-gel precursors.

The core of the nanocapsules in accordance with the present invention is preferably substantially free of the metal oxide which originates from the sol-gel precursor (as residual impurity). Further, the metal oxide shell is preferably substantially free of the core material constituents (as residual impurity). By the term "substantially free" is meant that the residual impurity has a concentration (w/w) of up to 10% (w/w), preferably up to 5% (w/w), more preferably up to 1% (w/w) even more preferably up to 0.5% (w/w).

According to a further embodiment, the core material comprises at least one active ingredient.

In the present invention, the term "active ingredient" refers to any molecule or substance that can be used in agriculture, industry (including food industry), medicine, cosmetics, and which grants the final product (cosmetics, drug, etc.) at least one desired property.

Thus the nanocapsules according to the present invention may be useful for oral administration, parenteral administration (e.g. intravenous, intramuscular, subcutaneous), topical administration, ophthalmic administration, etc.

According to one embodiment the core material consists essentially of at least one active ingredient.

As used herein the term "consists essentially of at least one active ingredient" means that the core material comprises a high percentage (w/w) of an active ingredient and low percentage of excipients (such as the liquid carrier). In certain embodiments the concentration of the active ingredient based on the total weight of the core material is above 80% w/w, more preferably above 90% w/w and most preferably above 95% w/w. The term "consists essentially of an active ingredient" also means that the core material may also include excipients which are needed for the preparation of the nanocapsules or to dissolve the active ingredient. Preferably the concentration of the excipients based on the total weight of the core material is up to 20% w/w, more preferably up to 10% w/w and most preferably up to 5% w/w.

According to another embodiment the core material is said at least one active ingredient (i.e. does not include excipients such as a liquid carrier).

In certain cases, where the active ingredient is an oil such as a sunscreen agent and additional excipients such as solvents or co-solvents are not needed in order to prepare the oily phase of the emulsion described in the process below, in this case the core material of the formed nanocapsules is the active ingredient.

In other application, for example when the active ingredient is a dye it will be advantages to dissolve the active ingredient (dye) in a solvent at a concentration of a dye which is sufficient to grant the desired color property. In this case the core material comprises an excipient preferably an oily solvent and the active ingredient (dye).

According to one embodiment the core is a liquid core and more preferably the liquid core is an oily core (i.e. a non-aqueous water immiscible liquid). The liquid core, preferably oily core may be for example in the form of a solution, suspension or dispersion.

The active ingredient may be present in a dissolved, dispersed or suspended form in the core (i.e. the active ingredient may be present in a dissolved, dispersed or suspended form in the excipients used to prepare the core material of the nanocapsules).

The nanocapsules may be useful for cosmetic or pharmaceutical applications. The nanocapsules may also be used in agricultural, polymeric or food industry. The nanocapsules may be useful for any application wherein the active ingredient should be isolated, temporarily or permanently from the ambient surroundings.

The active ingredient may be any molecules or substances that are soluble or that can be suspended in the sol-gel precursor (metal or the semi metal alkoxides) of choice.

The active ingredient may be for example sunscreen agents, dental agents, fragrances, perfume, colors and dyes, food colors and food additives, waxes, antioxidants, humidifiers, vitamins, pesticides, biological molecules (such as enzymes, co-enzymes or antibodies), drugs, catalysts, reagents or mixtures thereof.

The drugs may be for example dermatological agents, anti-inflammatory agents, analgesics, anti-fungal agents, antibiotics, anti-viral agents, anti-acne agents, anti histamines, skin whitening agents, anti-parasitic agents, muscle relaxants, steroids, hormones, astringents or mixtures thereof.

The active ingredient may be for example a pesticide such as insecticides, herbicides or fungicides used in agriculture or industry.

The active ingredient may be a sunscreen agent.

The sunscreen agent may be for example a UVA absorber, a UVB absorber, or mixtures thereof.

The UVA absorber may be for example octylmethoxy cinnamate, p-aminobenzoic acid, or mixtures thereof.

The UVB absorber may be for example 3-butylmethoxydibenzoyl methane, benzophenone-3 or mixtures thereof.

The sunscreen agent (ultra-violet absorbing molecules or ultra-violet reflecting substances) may be, for example, octylmethoxy cinnamate, 3-butylmethoxydibenzoyl methane, benzophenone-3, benzophenone-1, benzophenone-2, benzophenone-6, benzophenone-4, benzophenone-8,2-ethylhexyl p-methoxycinnamate, p-aminobenzoic acid, 2-ethylhexyl N,N-dimethyl-p-aminobenzoate, 2-cyano-3,3-diphenylacrylic acid 2-ethylhexyl ester, 2-ethylhexyl-2-cyano-3,3-diphenylacrylate, oxybenzone, 2-phenylbenzimidizole-5-sulfonic acid, homomethyl salicylate, octyl salycilate, 4,4'-methoxy-t-butyldibenzoylmethane, 4-isopropyl dibenzoylmethane, 3-(4-methylbenzyledene) camphor, 3-benzylidene camphor, triethanolamine salicylate, 4-N,N-(2-ethylhexyl)methyl aminobenzoic acid ester of 2,4-dihydroxybenzophenone, 4-N,N-(2-ethylhexyl)methyl aminobenzoic acid ester of 4-hydroxydibenzoylmethane, 4-N,N-(2-ethylhexyl)methyl-aminobenzoic acid ester of 2-hydroxy-4-(2-hydroxyethoxy)-benzophenone, 4-N,N-(2-ethylhexyl)methyl aminobenzoic acid ester of 4-(2-hydroxyethoxy)dibenzoylmethane, or mixtures thereof.

Additional sunscreen agents which may be used in the present invention are disclosed in U.S. Pat. Nos. 6,238,650, 6,468,509, 6,303,149, 6,436,375 and International Publication WO 03/039510. The disclosures of these patents and publications are incorporated herein by reference in their entirety.

The active ingredient may be for example natural food colors or synthetic food colors or food additives used in food products or oral drugs.

The active ingredient may be for example natural food colors or synthetic food colors used in cosmetic colors and skin applications.

According to one preferred embodiment the active ingredient is a dye.

The active ingredient may be for example a dye such as a fluorescent dye.

The fluorescent dye may be used in cosmetics, pharmaceutics, inks or any other industries where it is necessary to avoid the contact of the dye with its dispersing environment or with the different organs of the human body (such as the skin).

The fluorescent dye may be for example nile red, perylene, pyrene, antracene, or mixtures thereof.

According to a preferred embodiment of the present invention the nanocapsules have a particle size distribution of: d10=10-30 nm, d50=30-150 nm, d90=70-300 inn, in diameter. According to another preferred embodiment the nanocapsules have a particle size distribution of: d10=10-30 nm, d50=30-100 nm, d90=70-200 nm, in diameter. Further according to a preferred embodiment the nanocapsules have a particle size distribution of: d10=10-30 nm, d50=30-100 nm, d90=70-180 nm. Additionally according to a preferred embodiment the nanocapsules have a particle size distribution of: d10=10-30 nm, d50=30-100 nm, d90=70-160 nm. Moreover according to a preferred embodiment the nanocapsules have a particle size distribution of: 10-30 nm, d50=30-100 nm, d90=70-150 nm.

It is appreciated that the nano-emulsion particle size distribution obtained in (b) is similar to the particle size distribution of the nanocapsules. Thus, the particle size distribution (d10, d50, d90) of the nono-emulsion may have the same values as indicated in the present invention with respect to the nanocapsules.

According to an additional embodiment of the present invention the process further comprising chemically modifying the surface of the metal oxide shell.

According to a further embodiment of the present invention the chemical surface modification comprises reacting silanol groups on the surface of the metal oxide shell with precursors having the formula $(R^1)Si(OR'')_3$, $(R^1)(R^2)Si(OR'')_2$, $(R^1)(R^2)(R^3)Si(OR'')$, wherein $R^1$, $R^2$, $R^3$ may be the same or different and are independently selected from $C_1$-$C_{18}$alkyl, aryl, aryl $C_1$-$C_{18}$alkyl, $C_1$-$C_{18}$alkyl amine, $C_1$-$C_{18}$alkyl methacrylate, allyl, vinyl, $C_1$-$C_{18}$alkyl ester, acryloxy, allyloxy, aryloxy, carboxy$C_1$-$C_{18}$alkyl, halo$C_1$-$C_{18}$alkyl, $C_1$-$C_{18}$alkyl (C=O)—O—, cyano$C_1$-$C1_8$alkyl, epoxycycloalkyl, glycidoxy$C_1$-$C_{18}$alkyl, methacryloxy, $C_1$-$C_{18}$alkylthiol.

Whenever a numerical range e.g. "1-18" is stated herein in connection with an alkyl group, it means that the group in this case the alkyl group, may contain carbon atom, 2 carbon atoms, 3 carbon atoms, etc., up to and including 18 carbon atoms.

According to a preferred embodiment the $C_1$-$C_{18}$alkyl is a $C_1$-$C_6$ alkyl (e.g. methyl, ethyl, propyl etc.).

The $C_1$-$C_{18}$alkyl methacrylate may be for example methyl methacrylate, ethyl methacrylate, propyl methacrylate, etc.

The aryl may be for example a phenyl or benzyl.

The halo group may be for example chloro, fluoro, etc.

The carboxy $C_1$-$C_{18}$alkyl may be for example carboxymethyl, carboxyethyl, carboxypropyl, etc.

The cycloalkyl in the epoxycycloalkyl may be a 5-6 membered ring, such as epoxycyclopentyl or epoxycyclohexyl.

The glycidoxy$C_1$-$C_{18}$alkyl may be for example glycidoxypropyl.

OR" is preferably selected from $C_1$-$C_6$alkoxy, an aryloxy, a carboxylic ester, an acyloxy group, a halo (e.g. chloro or bromo).

$R^1$, $R^2$, $R^3$ preferably does not undergo hydrolysis in the conditions used to conduct the chemical modification of the metal oxide surface.

Such surface modification with functional groups $R^1$, $R^2$, $R^3$ is preferably carried out by a further step comprising:

reacting the nanocapsules obtained in step (c) with a precursor as defined above in an aqueous medium having a pH in the range of 2-7, more preferably 2-4. The reaction is preferably mixed (e.g. by mechanical stirring or magnetically stirring) for a period of e.g. 4-24 hours. An indication for the completion of the reaction can be obtained by constant loss on drying measurements of a sample of the nanocapsules taken at various time intervals.

The invention additionally relates to product obtained by the process as described in the present invention.

The invention further relates to nanocapsules having a core material encapsulated within a nanocapsular shell, the nanocapsular shell comprises at least one metal oxide, wherein the nanocapsules have a particle size distribution of: d10=10-80 nm, d50=30-200 nm, d90=70-500 nm, in diameter.

According to one preferred embodiment, the nanocapsules have a particle size distribution of: d10=10-30 nm, d50=30-150 nm, d90=70-300 nm, in diameter.

According to another preferred embodiment the nanocapsules have a particle size distribution of: d10=10-30 nm, d50=30-100 nm, d90=70-200 nm.

Further according to a preferred embodiment the nanocapsules have a particle size distribution of: d10=10-30 nm, d50=30-100 nm, d90=70-180 nm. Additionally according to a preferred embodiment the nanocapsules have a particle size distribution of: d10=10-30 nm, d50=30-100 nm, d90=70-160 nm. Moreover according to a preferred embodiment the nanocapsules have a particle size distribution of: 10-30 nm, d50=30-100 nm, d90=70-150 nm.

According to a preferred embodiment of the present invention the difference between d90 and d10 (d90-d10) is preferably in the range 50-300 nm, more preferably in the range 50-250 nm, even more preferably in the range 50-200 nm, and most preferably in the range 50-150 nm.

Preferably the core material comprises at least one active ingredient.

According to one embodiment the active ingredient is selected from sunscreen agents, dental agents, fragrances, perfume, colors and dyes, food colors, food additives, waxes, antioxidants, humidifiers, vitamins, pesticides, biological molecules, drugs, catalysts, reagents, and mixtures thereof.

According to a further embodiment the metal oxide is selected from silica, titania, alumina, zirconia, ZnO.

The shell may be further modified by functional groups selected from $C_1$-$C_{18}$alkyl, aryl, aryl $C_1$-$C_{18}$alkyl, $C_1$-$C_{18}$alkyl amine, $C_1$-$C_{18}$alkyl methacrylate, halo$C_1$-$C_{18}$alkyl, allyl, vinyl, $C_1$-$C_{18}$alkyl ester, acryloxy, allyloxy, aryloxy, carboxy$C_1$-$C_{18}$alkyl, $C_1$-$C_{18}$alkyl(C=O)—O—, cyano$C_1$-$C_{18}$alkyl, epoxycycloalkyl, glycidoxy$C_1$-$C_{18}$alkyl, methacryloxy, $C_1$-$C_{18}$alkylthiol.

It is appreciated that the nanocapsules constituents, concentrations of the constituents, specific active ingredient, and other parameters and characteristics may be as described in the present invention with respect to the process, product obtained by the process, etc.

The invention additionally relates to a composition comprising nanocapsules as described in the present invention and a carrier.

The nanocapsules of the present invention may be useful for human or non-human applications, as they may be easily incorporated in various carriers. The nanocapsules may be easily dispersed or suspended in a carrier or diluent.

Simple mixing with any suitable mixer or stirrer is sufficient to achieve an effective dispersion. If necessary, due to the small particle size distribution of the nanocapsules, high shear forces may be applied to facilitate fast and efficient mixing of the nanocapsules in the carrier.

The composition may be for example a cosmetic composition, a pharmaceutical composition, a food composition, a composition used in agriculture or industrial processes.

The carrier may be a cosmetic carrier, a pharmaceutical carrier, a food carrier, a carrier used in agriculture or industrial processes.

The carrier may be a liquid, a semi solid or a solid carrier. The carrier may be for example an emulsion, a cream, an aqueous solution, an oil, an ointment, a paste, a gel, a lotion, a milk, a suspension, a powder, a processed food, a spray, a paint, a lacquer, a coating, a plastic or a detergent.

The carrier may further comprise at least one non-encapsulated active ingredient.

The final form of the composition may be for example an emulsion, an aqueous solution, an oil, a semi-solid formulation (such as a cream, an ointment, a paste, or a gel), a lotion, a milk, a suspension, a powder, a capsule, an aerosol, a spray, a foam, a shampoo, a hair conditioner, a lacquer, a makeup, a solid stick, a toothpaste, a food, a paint, a plastic or a coating.

According to one embodiment the composition is a suspension of said nanocapsules in an aqueous medium.

According to a preferred embodiment the suspension comprises low surfactants concentration based on the nanocapsule's weight.

By the term "low surfactants concentration based on the nanocapsule's weight" is meant a concentration of preferably up to 5% w/w, more preferably up to 2% w/w and most preferably up to 0.5% w/w based on the total weight of the nanocapsules.

According to a preferred embodiment the composition is a suspension of said nanocapsules in an aqueous medium substantially free of surfactants.

According to a specific embodiment the suspension is physically stable for a period of at least 3 month, preferably for 1 year and more preferably for 3 years, at ambient temperature.

Further, according to another embodiment the composition is a dispersion of the nanocapsules in a liquid or semi-solid carrier and said composition is physically stable for a period of at least 3 month, preferably for 1 year and more preferably for 3 years, at ambient temperature. The composition may be substantially free of surfactants. Alternatively the composition may comprise low surfactants concentration based on the nanocapsule's weight.

By the term "physically stable" is meant an increase of up to 30%, preferably up to 20%, more preferably up to 10% and most preferably up to 5%, in d10, d50, and d90 parameters.

The compositions of the present invention may be applied topically.

In the present invention, the term "topical application" refers to an application on the skin, hair, mucous membranes, rectal application, nasal application, as well as dental application within the oral cavity.

The release of the active ingredient from the nanocapsules can be designed to be immediate, delayed, or controlled; this can be controlled by varying the composition of the nanocapsular shell, its diameter, and by varying the composition of the carrier surrounding the nanocapsules.

Release can be obtained and controlled by aging time, thermal treatment, or any mechanical mean that can change the characteristic porosity or strength of the shell, or by chemical means such as organic polymers and/or surfactants that may be added while the nanocapsules are being formed, to control the surface nature of the shell and the rate of diffusion through the pores.

Since the encapsulation creates micro-domains within the entire formulation, one active ingredient can be encapsulated while a second active ingredient can be present in the carrier that surrounds the nanocapsules. This is advantageous when the ingredients acts synergistically together, yet one is chemically reactive with another.

Alternatively each of the active ingredients may be nano-encapsulated in separate nanocapsules.

In an alternative, the active ingredient may be encapsulated alone, or with other ingredients within the same nanocapsule. Co-encapsulation of compounds that enhance stability of the sensitive ingredient is beneficial. For example, anti oxidants can be co-encapsulated with oxygen-sensitive or oxidant-sensitive ingredients, to provide "localized protection".

It should be understood that the invention is not limited in its application to the details of construction and the arrangement of the components set forth in the following description. The invention includes other embodiments and can be practiced or implemented in various ways. Also, it is to be understood that the phraseology and terminology employed herein is for the purpose of description only and should not be regarded as limiting.

EXAMPLES

The following examples clarify and demonstrate the present invention. They are not under any circumstances exclusive and do not intend to limit the scope of the present invention.

Example 1: Nanometric Core Shell Particles of Oil

Example 1a: Nanometric Core Shell Particles of Paraffin Oil 400 g of paraffin oil and 70 g of TOES (tetraethoxysilane) were added to a solution of 405 g of water containing 5 g of CTAC (29% w/w). The mixture was homogenized by high shear homogenizer using Polytron 6100 By KINEMATICA for 5 minutes at 3500 rpm. The emulsion was milled by microfluidizer at a temp of 7° C. (M-110Y microfluidizer processor) at three portions, each one for 10 minutes to obtain nano-emulsion. The nano-emulsion was transferred to stainless vessel adapted with mechanical stirrer, and 100.2 g of water containing 0.2 g of HCl (1N) were added to the nano-emulsion. The nano-emulsion was stirred at 35° C. for 20 hours to obtain nano-capsules having an oil core and silica shell.

The capsule had a particle size distribution of d(0.9)=146 nm, d(0.5)=84.2 nm, d(10)=26.4 nm by volume (FIG. 1a) (measured with Zetasizer Nano Z Malvern) and the solid content was 27.3% w/w (solid content refers to the non-volatile ingredients, based the total weight of the aqueous dispersion of the nanocapsules).

Example 1b: Nanometric Core Shell Particles of IPM (Isopropylmyristate)

20 g of IPM and 20 g of TOES were added to a solution of 95 g of water containing 5 g of CTAC (29%). The mixture was homogenized by high shear homogenizer (using Polytron 6100 By KINEMATICA) for 5 minutes at 2800 rpm. The emulsion was milled by microfluidizer at a temp of 7° C. for 10 minutes to obtain nano-emulsion. 150 g of water were added to the nano-emulsion and the milling continued for 5 more min. The nano-emulsion was stirred at room temp. for 20 hours after addition of 0.5 ml of 1M HCl solution to obtain nano-capsules having an IPM oil core and silica shell. The capsule had a particle size distribution of d(0.9)=215 nm, d(0.5)=126 nm, d(0.1)=71 nm. Particle size distribution was measured with mastersizer 200 (Malvern) by volume.

Example 2: Nanometric Core-Shell Particles with Paraffin Oil and Nile Red Core 0.02 g of Nile Red was dissolved in 20 g paraffin oil by heating (to a temp of 60° C.) and stirring for 30 min. 20 g of TEOS were added to the hot solution and the mixture was stirred for another 30 min. The bright orange solution was cooled to room temperature. A solution of 0.5-2% w/w of CTAC was prepared. The oil phase and the CTAC solution were homogenized using a high shear homogenizer (Polytron PT 6100 Kinematica) with dispersing aggregates PT-DA 6045/6 in 3000 rpm for about 5 min in a long neck beaker (200 ml). During homogenization the emulsion color has changed from bright orange to purple. The emulsion was sheared for 10 min. in M-110Y microfluidizer processor (microfluidics) at a temp of 7° C. to obtain nano-emulsion. 150 g RO (reverse osmosis) water was added and the emulsion was sheared for additional 5 min. After the shearing the nano-emulsion was transferred to a 400 ml beaker equipped with magnetic stirrer. 0.5 ml of 1M HCl solution were added as catalyst and the nano-emulsion was stirred for 24 h to form nanometric capsules having a core/shell structure.

Figure 1B:
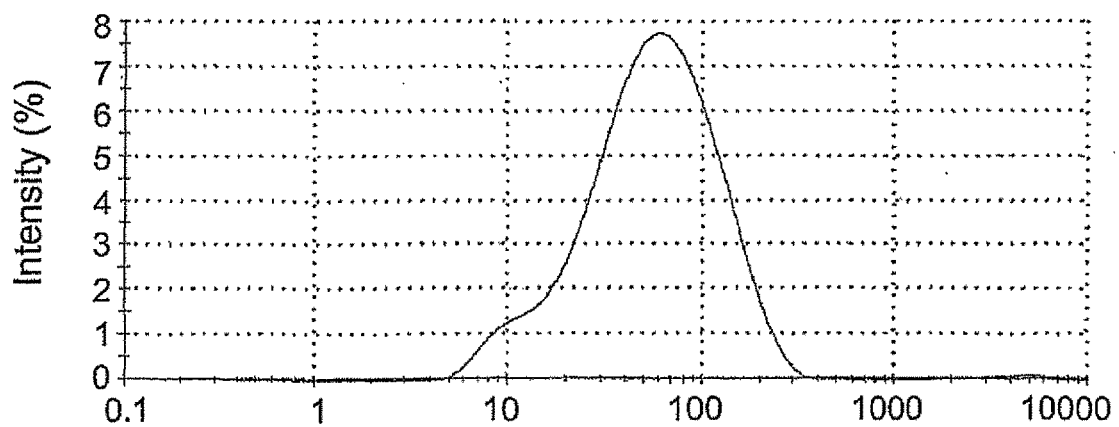

The particle size distribution (PSD) of the nanometric capsules obtained was d(0.9)=120.6 nm d(0.5)=67.9 nm d(0.1)=16.7 nm by volume, measured with Zetasizer Nano Z Malvern (FIG. 1b) and the solid content was 10.27% w/w.

PSD was also measured by Mastersizer 2000 (Malvern) and the results were: d(0.9)=190 nm d(0.5)=112 nm d(0.1) =68 nm, and d(0.9)=181 nm, d(0.5)=120 nm, d(0.1)=79 nm.

Figure 2A:
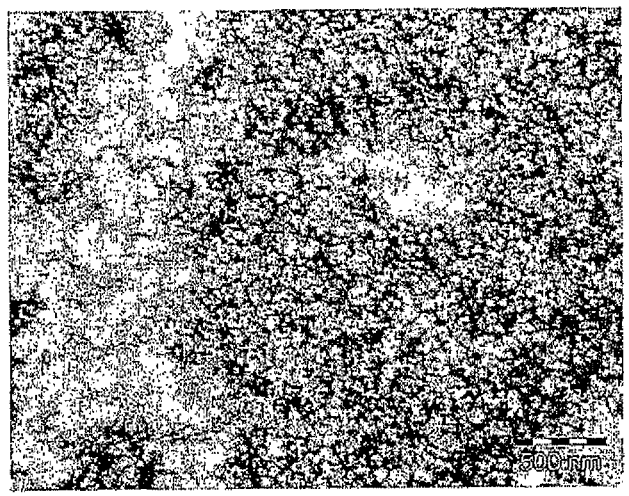
FIG. 2a shows that the particles obtained are in the nanometric range and FIG. 2b shows a clear core-shell structure.
Figure 2B:
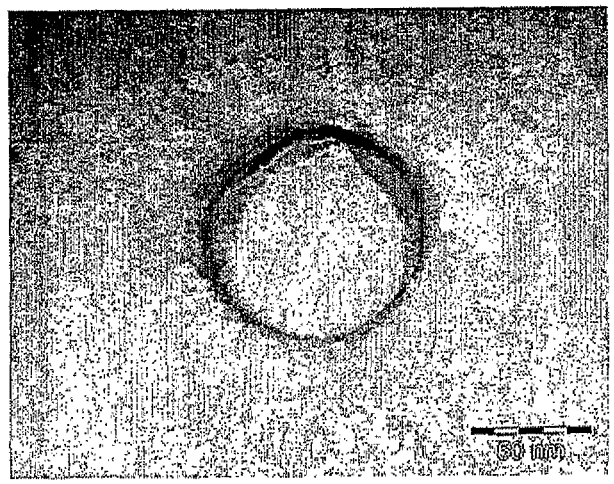

The nanometric core-shell particles were analyzed by transmission electron microscope (TEM) as seen in the pictures shown in FIG. 2. FIG. 2a shows the nanocapsules obtained. A core shell structure of the nanometric particles can be observed having a silica shell thickness of about 4-8 nm as shown in FIG. 2b.

Example 3: Modification of the Nanometric Capsules with Acrylate Function 1.5 g of 3-(trimethoxysillyl)propylmethacrylate were added to 100 g of nanometric capsules dispersion obtained in example 2 with vigorous stirring of up to 1000 rpm. The dispersion was stirred for 24 h. The particles size distribution (PSD) after the modification was about d(0.9)=210 nm, d (0.5)=104.6 nm, d(0.1)=40.0 nm.

Example 4: Encapsulation of UV Absorber in Nanometric Capsules 1 g of Tinuvin 326 (UV absorber) were dissolved in 19 g of IPM (isopropylmyristate) by heating (to a temperature of 60° C.). 20 g of TEOS were added and the solution was cooled to room temperature. The oil phase was homogenized with water solution of CTAC (5 g CTAC 29% w/w and 95 g RO water) using a high-shear homogenizer (Polytron PT 6100 Kinematica) with dispersing aggregates PT-DA 6045/6 in 3000 rpm for about 5 min in a long neck beaker (200 ml). The fine emulsion was sheared for 10 min. in M-110Y microfluidizer processor (microfluidics). 150 g RO water were added and the emulsion was sheared for additional 5 min. After the shearing the nano-emulsion was transferred to 400 ml beaker equipped with magnetic stirrer. 0.5 ml of 1M HCl solution was added as catalyst and the nano-emulsion was stirred for 24 h. The nanometric capsules had a PSD of about d(0.9)=160 nm, d(0.5)=90 nm, d(0.1)=46 nm (measured with Zetasizer Nano Z Malvern).

Example 5: Encapsulation of UV Absorber and Fluorescent Dye in Nanometric Core-Shell Particles 0.5 g Tinuvin 326 and 0.015 g Nile Red was dissolved in hot (at temp of 60° C.) IPM (19.5 g). 20 g of TEOS were added and the oil phase was cooled to room temperature. The oil phase was homogenized with water solution of CTAC (5 g CTAC 29% w/w and 95 g RO water) using a high-shear homogenizer (Polytron PT 6100 Kinematica) with dispersing aggregates PT-DA 6045/6 in 3000 rpm for about 5 min in a long neck beaker (200 ml). The fine emulsion was sheared for 10 min. in M-110Y microfluidizer processor (microfluidics). 150 g RO water were added and the emulsion was sheared for additional 5 min. After the shearing the nano-emulsion was transferred to 400 ml beaker equipped with magnetic stirrer. 0.5 ml of 1M HCl solution was added as catalyst and the nano-emulsion was stirred for 24 h.

The PSD was measured by Mastersizer 2000 (Malvern) and the results were: d(0.9)=255 nm, d(0.5)=137 nm, d(0.1) =73 nm.

Example 6: Encapsulation of Preservatives in Nanometric Core-Shell Particles 4 g (20%) phenonip (mixture of phenoxyethanol, methylparaben, ethylparaben, propylparaben, butylparaben and isobutylparaben) were dispersed in IPM (16 g). 20 g of TEOS were added to the oil phase at room temperature. The oil phase was homogenized with water solution of CTAC (4 g CTAC 29% and 96 g RO water) using a high-shear homogenizer (Polytron PT 6100 Kinematica) with dispersing aggregates PT-DA 6045/6 in 3000 rpm for about 5 min in a long neck beaker (200 ml). The fine emulsion was sheared for 10 min. in M-110Y microfluidizer processor (microfluidics). 150 g RO water were added and the emulsion was sheared for additional 5 min. After the shearing the nano-emulsion was transferred to 400 ml beaker equipped with magnetic stirrer. 0.5 ml of 1M HCl solution was added as catalyst and the nano-emulsion was stirred for 24 h.

The PSD was measured by Mastersizer 2000 (Malvern) and the results were: d(0.9)=290 nm, d(0.5)=137 nm, d(0.1)=67 nm.

Example 7: Additionally of Silica Precursor in the Continuous Phase 200 g of paraffin oil are added to a solution of 305 g of water containing 3 g of CTAC (29% w/w). The mixture is homogenized by high shear homogenizer for 5 minutes. The emulsion is milled by microfluidizer for 10 minutes to obtain nano-emulsion. The nano-emulsion is transferred to stainless vessel adapted with mechanical stirrer. 50 g of TEOS are added to the nano-emulsion and the mixture is mixed for 30 min. 100.2 g of water containing 0.2 g of HCl (1N) are added to the nano-emulsion. The nano-emulsion is stirred at 35° C. for 20 hours to obtain nano-capsules having an oil core and silica shell.

Example 8: Nanocapsules Having Titania Shell 300 g of paraffin oil and 50 g of Tri propoxy titanate are added to a solution of 405 g of water containing 3 g of CTAC (29% w/w). The mixture is homogenized by high shear homogenizer for 5 minutes. The emulsion is milled by microfluidizer for 10 minutes to obtain nano-emulsion. The nano-emulsion is transferred to stainless vessel adapted with mechanical stirrer. 100.2 g of water containing 0.2 g of HCl (1N) are added to the nano-emulsion. The nano-emulsion is stirred at 4° C. for 20 hours to obtain nano-capsules having an oil core and silica shell.

Example 9: TMOS as Silica Precursor 400 g of paraffin oil and 100 g of TMOS (tetramethoxysilane) are added to a solution of 605 g of water containing 5 g of CTAC (29% w/w). The mixture is homogenized by high shear homogenizer for 5 minutes. The emulsion is milled by microfluidizer at three portions, each one for 10 minutes to obtain nano-emulsion. The nano-emulsion is transferred to stainless vessel adapted with mechanical stirrer, and the pH is adjusted to 6 using HCl (1N). The nano-emulsion is stirred at 4° C. for 20 hours to obtain nano-capsules having an oil core and silica shell.

Example 10: Stability of an Aqueous Suspension Prepared According Example 2

An aqueous suspension was prepared using the nanocapsules obtained according to Example 2. The aqueous suspension contained 10% w/w of the nanocapsules in water (without surfactants) as a medium.

The aqueous suspension was found to be stable for 3 months at ambient temperature, with about 10% increase in d10, d50, and d90 parameters.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

The invention claimed is:

1. A process for preparing nanocapsules having a core-shell structure, comprising:
   (a) preparing an oil-in-water emulsion by emulsification of an oily phase that comprises a core material in an aqueous phase under high shear forces at 1000-4000 rpm, wherein one or both of the oily phase and the aqueous phase comprise a sol-gel precursor;
   (b) subjecting the emulsion obtained in (a) to a high pressure homogenization in the range of 1300-1700 bar to obtain a nano-emulsion; and
   (c) applying conditions for hydrolyzing and polycondensing the sol-gel precursor to obtain nanocapsules having a metal oxide shell encapsulating the core material, wherein said nanocapsules have a narrow particle size distribution of: d10=10-80 nm, d50=30-200 nm, and d90=70-500 nm, in diameter.

2. The process of claim 1 wherein said oily phase comprises a core material and a sol-gel precursor.

3. The process of claim 1 wherein the emulsion obtained in step (a) comprises a median particle size diameter (d50) in the range of 1-10 μm.

4. The process of claim 3, wherein the emulsion in step (a) has a particle size distribution of: d10=0.5-5 nm, d50=1-10 nm, and d90=2-30 nm, in diameter.

5. The process of claim 1 wherein said core material comprises at least one active ingredient selected from the group consisting of sunscreen agents, dental agents, fragrances, perfume, colors and dyes, food colors, food additives, waxes, antioxidants, humidifiers, vitamins, pesticides, biological molecules, drugs, catalysts, reagents, and mixtures thereof.

6. The process of claim 1 wherein said sol-gel precursor is metal alkoxide monomers, semi-metal alkoxide monomers, metal ester monomers, semi-metal ester monomers, and/or monomers of the formula $M(R)_n(P)_m$, wherein M is a metallic or semi metallic element, R is a hydrolysable substituent, n is an integer from 2 to 6, P is a non polymerizable substituent and m is an integer from 0 to 6, a partially hydrolyzed and partially condensed polymer thereof.

7. The process of claim 6 wherein said metallic or semi metallic element is at least one selected from the group consisting of Si, Ti, Zr, Al, and Zn.

8. The process of claim 6 wherein said sol-gel precursor is at least one selected from the group consisting of silicon alkoxide monomers, silicon ester monomers, monomers of the formula $Si(R)_n(P)_m$, where R is a hydrolysable substituent, n is an integer from 2 to 4, P is a non polymerizable substituent and m is an integer from 0 to 2, a partially hydrolyzed and partially condensed polymer thereof, and any mixture thereof.

9. The process of claim 8 wherein said silicon alkoxide monomer is at least one selected from the group consisting of tetramethoxy silane, tetraethoxy silane, and mixtures thereof.

10. The process of claim 1 wherein the conditions in step (c) comprising adding a catalyst selected from the group consisting of an acid and a base.

11. The process of claim 1 wherein the conditions in step (c) comprise mixing and stirring said nano-emulsion with another aqueous solution at a suitably selected pH in the range of 2-13, to obtain nanocapsules in a suspension.

12. The process of claim 11 wherein the pH of the aqueous solution is in the range of 2-5.

13. The process of claim 1 wherein the pH of the aqueous phase is in the range 2-13.

14. The process of claim 13 wherein the pH of the aqueous phase is in the range 5-8.

15. The process of claim 1 wherein said nanocapsules have a particle size distribution of: d10=10-30 nm, d50=30-150 nm, and d90=70-300 nm, in diameter.

16. The process according to claim 1 further comprising chemically modifying the surface of the metal oxide shell.

17. The process of claim 16, wherein the chemical surface modification comprises reacting silanol groups on the surface of the metal oxide shell with precursors having the formula:

$(R^1)S_i(OR'')_3, (R^1)(R^2)Si(OR'')_2, (R^1)(R^2)(R^3)S_i(OR'')$, wherein $R^1$, $R^2$, and $R^3$ are the same or different and are independently selected from $C_1$-$C_{18}$alkyl, aryl, aryl $C_1$-$C_{18}$alkyl, $C_1$-$C_{18}$alkyl amine, $C_1$-$C_{18}$alkyl methacrylate, halo $C_1$-$C_{18}$alkyl, allyl, vinyl, $C_1$-$C_{18}$alkyl ester, acryloxy, allyloxy, aryloxy, carboxy $C_1$-$C_{18}$alkyl, $C_1$-$C_{18}$alkyl(C=O)—O—, cyano $C_1$-$C_{18}$alkyl, epoxycycloalkyl, glycidoxy $C_1$-$C_{18}$alkyl, methacryloxy, and $C_1$-$C_{18}$alkylthhiol.

18. A nanocapsule obtained by the process according to claim 1.

19. The process of claim 12 wherein the pH of the aqueous solution is in the range of 3-4.

20. A textile fiber, a cosmetic composition or a pharmaceutical composition comprising a matrix, an aqueous solution or combination thereof; wherein the matrix, aqueous solution or combination thereof comprise nanocapsules having a core-shell structure; wherein the nanocapsules are prepared according to the process of claim 1; and the matrix, aqueous solution or combination thereof is free of surfactant.

* * * * *